United States Patent [19]

Dairaku

[11] Patent Number: 4,865,995
[45] Date of Patent: Sep. 12, 1989

[54] METHOD FOR MEASURING A CONCENTRATION OF SACCHARIDES HAVING A LOW MOLECULAR WEIGHT AND SENSOR FOR MEASURING THE SAME

[75] Inventor: Kazuo Dairaku, Kobe, Japan

[73] Assignee: Kanegafuchi Kagaku Kogyo Kabushiki Kaisha, Osaka, Japan

[21] Appl. No.: 826,038

[22] Filed: Feb. 4, 1986

[30] Foreign Application Priority Data

Feb. 4, 1985 [JP] Japan .................................. 60-19715

[51] Int. Cl.$^4$ ............................................. G01N 30/96
[52] U.S. Cl. ........................................ 436/94; 422/68; 422/69; 435/288; 435/299; 435/311; 436/95; 436/178
[58] Field of Search ................... 436/501, 514, 529, 94, 436/95, 178, 536, 178; 435/288, 299, 311, 7; 422/68, 69

[56] References Cited

U.S. PATENT DOCUMENTS

| | | | |
|---|---|---|---|
| 4,073,713 | 2/1978 | Newman | 435/288 X |
| 4,344,438 | 8/1982 | Schultz . | |
| 4,429,122 | 1/1984 | Zupancic | 536/124 |
| 4,705,503 | 11/1987 | Dorman et al. | 604/53 X |

OTHER PUBLICATIONS

Schultz et al, Biotechnology and Bioengineering Symp. 9, pp. 65–71 (1979).
Schultz et al, Diabetes Care, 5(3), pp. 245–253 (May–Jun. 1982).
Mansouri et al, Bio/Technology, pp. 885–890 (Oct. 1984).
Srinivasan et al, Biotechnology and Bioengineering, 28, pp. 233–239 (1986).
Schultz, Biomedical Applications. Synthetic Membranes: Science, Engineering and Applications, pp. 647–665 (1986).
The Merck Index, Merck & Co., Rahway, N.J., (1983), pp. 426, 780.

*Primary Examiner*—Christine M. Nucker
*Assistant Examiner*—Jill Johnston
*Attorney, Agent, or Firm*—Armstrong, Nikaido, Marmelstein, Kubovcik & Murray

[57] ABSTRACT

A method for measuring the concentration of low molecular weight saccharides in a liquid by placing the liquid in contact with one side of a membrane which allows saccharides to pass through, but not polysaccharides. A detecting liquid containing polysaccharides is placed in contact with the other side of the membrane. The detecting liquid is also in contact with a ligand which has a higher affinity for the saccharides than for the polysaccharides. The concentration of saccharides is calculated from the measured change in the concentration of polysaccharides in the detecting liquid. A sensor for measuring the concentration of low molecular weight saccharides based on the same method is also described.

11 Claims, 3 Drawing Sheets

METHOD FOR MEASURING A CONCENTRATION OF SACCHARIDES HAVING A LOW MOLECULAR WEIGHT AND SENSOR FOR MEASURING THE SAME

BACKGROUND OF THE INVENTION

The present invention relates to a method for measuring the concentration of saccharides having a low molecular weight and a sensor for measuring the same, especially of the saccharides which are difficult to determine by on line or continuous measurement.

Measuring the concentration of saccharides having a low molecular weight such as glucose, fructose, saccharose and syrup has an increasing importance in various fields.

In the field of medical treatment and examination, it is important to measure the concentration of glucose in blood, i.e., blood sugar level and for a serious case of diabetes requiring an insulin administration, the blood sugar level should be measured automatically in order for the proper amount of insulin to be administered.

In the field of fermentation industry, the concentration of a syrup (a mixture of a low molecular weight sugar such as glucose, fructose or saccharose), which is a nutrient source of microorganisms should always be measured. Also in the field of food industry the measurement of glucose, fructose or saccharose is very important to quality control.

For such requirement in various fields, varieties of a sensor for measuring the concentration of saccharides have been provided. Though a method measuring the refractive index was first proposed, it had a disadvantage in selectivity in saccharides to be measured and thus was replaced by a sensor for measuring the concentration of saccharides, especially glucose, employing immobilized enzymes or immobilized microorganisms. The sensor for measuring the concentration of glucose utilizing the immobilized enzyme or immobilized microorganisms is based on the change of concentration of hydrogen peroxide of oxygen produced by oxidation of glucose by glucoseoxygenase which is immobilized on the membrane. Since the sensor can measure a very small amount of glucose and has a high selectivity, it is partly put to practical use.

However, such sensor employing the immobilized enzymes or immobilized microorganisms has a drawback in that a change of an activity of the enzymes or a change of generating power of the sensor due to the clogging of the membrane wherein the enzymes and the like is immobilized occurs with the lapse of time. Therefore, gain and base should be renewed with each sample and every short time and this makes it difficult to measure continuously.

Further, it is required to sterilize the instruments for using in the field such as medical treatment or examination fermentation industry or food industry. However, the sterilization cannot sufficiently be carried out when the material containing enzyme or microorganism is employed.

SUMMARY OF THE INVENTION

The object of the present invention is to provide a method and a sensor for measuring the concentration of saccharides having a low molecular weight which can measure continuously or intermittently as well as individually.

Another object of the present invention is to provide a sensor for measuring the concentration of saccharides having a low molecular weight which can be sterilized.

Other objects of the present invention will be made apparent from the following description.

According to the present invention, a method is provided for measuring the concentration of saccharides having a low molecular weight in a liquid to be measured, which comprises arranging the liquid to be measured and a detecting liquid including polysaccharides respectively on each node of a membrane which allows the saccharides having a low molecular weight to pass through but not the polysaccharides, transferring the saccharides having a low molecular weight through the membrane due to the concentration difference of the saccharides having a low molecular weight in the two liquids, and measuring the concentration of the polysaccharides, which are in an adsorption-desorption equilibrium in the detecting liquid owing to a difference in affinity for a ligand between the polysaccharides and the saccharides having a low molecular weight. Also provided is a sensor for measuring the concentration of the saccharides having a low molecular weight by utilizing the above method.

DETAILED DESCRIPTION OF THE INVENTION

Figure 1:
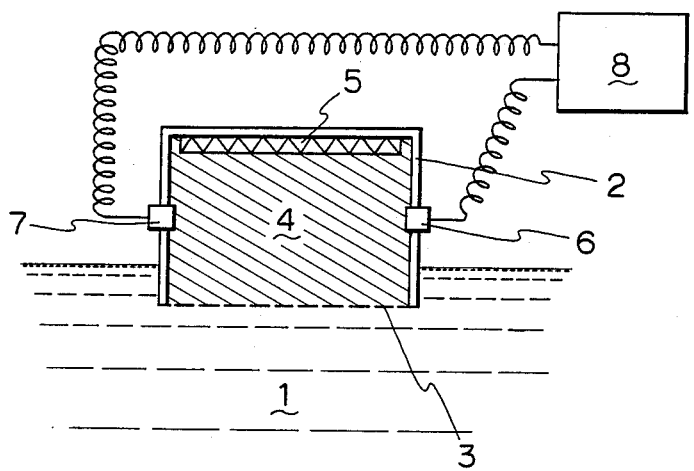
FIG. 1 shows an illustration of one embodiment of the sensor according to the present invention.

The method of the present invention is not based on directly measuring the concentration of the saccharides having a low molecular weight, which itself is difficult to be detected with a long-term stability. The method of the present invention comprises utilizing a ligand having an affinity for both the polysaccharides of a high molecular weight and the saccharides having a low molecular weight to be measured with the affinity for the saccharides to be measured being higher than the affinity for the polysaccharides, measuring the concentration of the polysaccharides which changes due to the adsorption-desorption activity of the ligand, and calculating the concentration of the saccharides having a low molecular weight from the measured concentration of the polysaccharides.

The method of the present invention is based on the following principles, i.e., the detecting liqiud containing a prescribed amount of the polysaccharides is enveloped with the membrane which alows the saccharides having a low molecular weight to pass through, but not the polysaccharides of a high molecular weight. First the ligand is contacted with the detecting liqiud so that the polysaccharides are absorbed to the ligand. Then the detecting liquid and the liquid to be measured containing the saccharides to be measured are arranged respectively on each side of the membrane and the saccharides having a low molecular weight to be measured is transferred into the detecting liquid through the membrane. The detecting liquid containing the transferred saccharides having a low molecular weight to be measured is contacted with the ligand so that the polysaccharides are desorbed and the saccharides to be measured are adsorbed due to the action of the ligand which has a higher affinity for the saccharides to be measured than for the polysaccharides which results in an increase in concentration of free polysaccharide in the detecting liquid. Consequently, by detecting the increase in concentration of the free poly-saccharides, the amount of the saccharides to be measured which are adsorbed to the ligand in place of the polysaccharides, or the concentration of the saccharides to be measured in the liquid to be measured, can be measured.

The term "free polysaccharides" in the present specification means the polysaccharides which are not adsorbed to or desorbed from the ligand.

The method of the present invention based on the above principle enables not only an individual measurement but also a continuous measurement or intermittent one since the polysaccharides are reversibly and rapidly adsorbed or desorbed depending on the concentration of the saccharides having a low molecular weight.

The free polysaccharides in the present invention can be detected, for instance, by measuring the absorption by means of an optical means for the free polysaccharides which can absorb or scatter, by measuring the conductivity for the free polysaccharides to which ion-releasing groups are incorporated, by measuring the capacitance due to a concentration change by measuring the viscosity change, or by mesuring the oxidation-reduction potential.

Though in the following description only a method for detecting the free polysaccharides by means of an optical means is described, and a case wherein the saccharides having a low molecular weight are transferred from the liquid to be measured to the detecting liquid is explained for simplification, the present invention is not limited to such a description. As the occasion demands the free polysaccharides may be detected by dissolving a predetermined amount of saccharides having a low molecular weight into the detecting liquid before measurement, transferring the saccharides having a low molecular weight to the liquid to be measured through the membrane, and measuring the concentration change of the free polysaccharides due to adsorption of the free polysacchrides, with a decreased amount of the saccharides having a low molecular weight in the detecting liquid.

The materials to be measured in the present invention are the saccharides having a low molecular weight, for instance, a molecular weight of not more than $1 \times 10^3$, which can scarcely be detected by means of an optical means. Examples of them are, for instance, glucose, fructose, saccharose, a mixture thereof, syrup, maltose, lactose, mannose and the like.

The method of the present invention is particularly effective when the saccharides to be measured are contained in an aqueous liqiud such as blood, culture broth, liquid food or the like.

The polysaccharides of the high molecular weight in the present invention which are detected by means of an optical means in place of the saccharides to be measured are those which can absorb or scatter and have less affinity for the ligand than the saccharides to be measured. The mean molecular weight of the polysaccharides may be such that it does not allow the polysaccharides to pass through the membrane and is, for instance, not less than $5 \times 10^3$, preferably from $1 \times 10^4$ to $5 \times 10^6$, most preferably from $1 \times 10^5$ to $3 \times 10^6$. Examples of the polysaccharides are, for instance, dextran, sulfonated dextran, cellulose having amino group and the like, preferably blue dextran having a mean molecular weight of about $2 \times 10^6$ wherein blue chromophore is covalently bonded to dextran.

In selecting the polysaccharides, it is also necessary to take into account the combination of the polysaccharides with the saccharides to be measured, as well as the condition as mentioned above.

The polysaccharides of a high molecular weight are preferably used in the form of an aqueous solution.

One of the characteristics of the method of the present invention lies in that the liquid to be measured and the detecting liquid including the polysaccharides are arranged respectively on each side of the membrane, and the saccharides having a low molecular weight to be measured in the liquid to be measured are transferred to the detecting liquid. Therefore, the membrane employed in the present invention should be such that it allows the saccharides having a low molecular weight to be measured to pass through, but not the polysaccharides of a high molecular weight. Examples of the membrane are, for instance, an ultrafiltration membrane, a dialyzer, a reverse osmosis membrane, and the like. Although the membrane may be in the microscopic structure of an isometric membrane or an asymmetric membrane, the asymmetric membrane is preferable since the migration speed of the saccharides through the asymmetric membrane is extremely higher than that through the isometric one. The membrane may be in the form of a flat membrane or a hollow fiber, preferably the membrane in the form of a hollow fiber is employed when a rapid measurement is required. If the liquid to be measured is colored, for example blood syrup, and the free polysaccharides are measured by the optical means, the membrane which does not permit a coloring matter in the liquid to migrate is preferable. The membrane is preferably made of regenerated cellulose, acetylcellulose, nitrocellulose, polyolefinpolymer, polycarbonate, polyfluoroethylene, high molecular weight electrolyte complex, polyaromatic sulphone, polysulphone, polyvinyl chloride, a copolymer of vinyl chloride and acrylonitrile, an aromatic high molecular weight compound such as polyaromatic amide, silicone rubber, polyester, a block copolymer of silicone and dimethylsilicone carbonate, or the like.

Any ligand can be employed in the present invention, which has an affinity for both the saccharides to be measured and the polysaccharides, with a higher affinity for the saccharides to be measured than for the polysaccharides, or in which an adsorption-desorption equilibrium is established and adsorption or desorption of the polysaccharides occurs depending on the concentration of the saccharides to be measured present in the detecting liquid.

Such ligand can be properly selected considering the combination of the saccharides to be measured with the polysaccharides and the like. Examples of the preferable ligand are, for instance, lectin, enzyme, antibody, nucleic acid, hormone, vitamine, cell and the like. When glucose is measured by employing dextran as the polysaccharide, preferably concanavalin A, or Lentil Lectin, Wheat germ Lectin or the like is used as the ligand.

The ligand to be used is preferably immobilized, more preferably to be covalently bonded to the insoluble support, which is preferably sepharose, sepharose derivative or the like. Further, the ligand may be immobilized to the support with a spacer between the ligand and the support.

For detecting the polysaccharides in the detecting liquid by means of an optical means, absorption, for instance, is measured in the conventional manner. Though the wave length to be measured may be selected as the occasion demands depending on the kind of the polysaccharides employed, it is important to select a wave length that does not detect the impurities.

The vessel employed in the present invention may be any which has at least one opening and can confine the detecting liquid by enveloping the opening.

The condition of the method of the present invention may be determined as the occasion demands depending on the kind of the saccharide to be measured and other components in the liquid to be measured which contains the saccharides to be measured.

For example, when the concentration of glucose in an aqueous solution of glucose is measured, and blue dextran is the polysacchairde, a membrane made of cellulose or cellulose derivative which allows the substrate having a molecular weight of not more than $1 \times 10^3$ to permeate the membrane, lectin is the ligand and a wavelength of 200 to 300 nm may be employed.

The concentration of the polysaccharides in the detecting liquid may be in the range from 5 to 0.01% (weight percent, hereinafter the same), usually 1 to 0.01%. In case of dextran, 0.5 to 0.01% of the concentration is usually employed.

Though the measuring range of the concentration of the saccharide to be measured in the liquid to be measured varies depending on the kind of saccharides to be measured or the like, the measurement can usually be carried out in the range of from 0.01 to 100 g/l, and in case of glucose, in the range from 0.01 to 100 g/l.

Though the pH value may vary, a pH of around 7.4 is employed when the ligand is concanavalin A. The regulation of the pH value can be carried out, for instance, by adding a buffer solution such as Tris-hydrochloric acid buffer to maintain the pH value or to adjust to an optimum pH value. Though the temperature is not particularly limited, it is preferably maintained at around 30° C.

In the method of the present invention, the ligand may be put in or immobilized in the vessel wherein the detecting liquid is confined. Alternatively, only the ligand may be immobilized on another site and the detecting liquid may be circulated through the ligand.

The present invention also relates to a sensor for measuring concentration by utilizing the method as mentioned above.

The preferable embodiments of the sensor of the present invention for measuring concentration are explained on the basis of the drawings. However, it should be understood that the present invention is not limited to such embodiments.

FIG. 1 is an illustration of one embodiment of the fixed type sensor according to the present invention. The liquid to be measured (1) contains the saccharides to be measured. The vessel (2) has an opening on one side. The opening of the vessel (2) is enveloped with the membrane (3) and in the space surrounded by the vessel (2) and the membrane (3) is confined the detecting liquid (4) containing the polysaccharides. The ligand (5) is immobilized on an inner wall of the vessel (2). Further the vessel (2) is equipped with the emission member (6) and the receiving member (7) wherein the emission member (6) and the receiving member (7) are arranged face to face at the proper distance and are connected to the detector (8) to constitute an optically detecting means.

For measuring the concentration of the saccharides to be measured in the liquid to be measured, it is enough that the member (3) installed with the vessel (2) is soaked in the liquid to be measured (1), after which the saccharides to be measured are transferred to the detecting liquid through the membrane and are absorbed to the ligand in place of the polysaccharides, thus causing the polysaccharides which were adsorbed to the ligand to desorb, which results in an increase of the concentration of the free polysaccharides in the detecting liquid. The increase in the amount of the free polysaccharides causes a decrease of light quantity of the specified wave length passing through the detecting liquid, which was emitted from the emission member (6) and was received at the receiving member (7). The data of the light quantity decrease (i.e., increase of absorbance) is transmitted to the detector (8), wherein the increase of the concentration of the free polysaccharides is calculated from the decrease of the light quantity passing through. From the increase of the concentration of the free polysaccharides the concentration of the saccharides to be measured is obtained, and thus the concentration of the saccharides to be measured in the liquid to be measured can be measured. In the case where the concentration of the saccharides to be measured in the liquid to be measured is decreased, the decrease in the opposite direction occurs and the concentration of the saccharides to be measured can also be measured in a similar way.

The sensor may be vibrated mechanically or by supersonic waves in order to accelerate the response rate.

Figure 2:
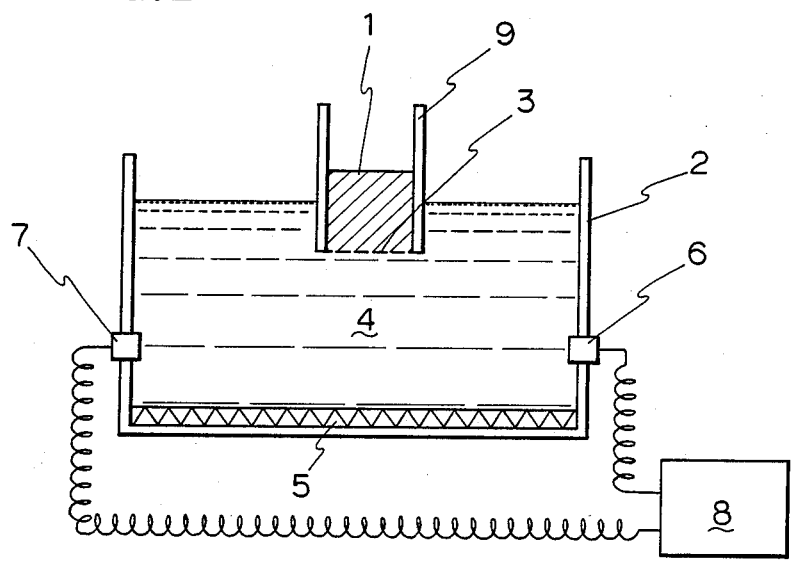
FIGS. 2 to 4 show illustrations of another embodiment of the sensor according to the present invention.

When a small amount of the liquid to be measured is employed, the sensor may be such that a predetermined amount of the detecting liquid (4) is filled in the vessel (2) equipped with the emission member (6) and the receiving member (7). The small vessel (9) which is enveloped with the membrane (3) at the opening and is charged with a specified amount of the liquid to be measured (1) is soaked in the detecting liquid (4), so that the membrane (3) is soaked in the detecting liquid (4), as shown in FIG. 2.

The sensor can be planted into the living body to measure the blood sugar level by miniaturization, wherein the blood sugar level can be measured in an automatic and continuous manner without a flow of electricity in the living body if the emission memeber (6) and the receiving member (7) are connected to the detector (8) with an optical fiber.

Figure 3:
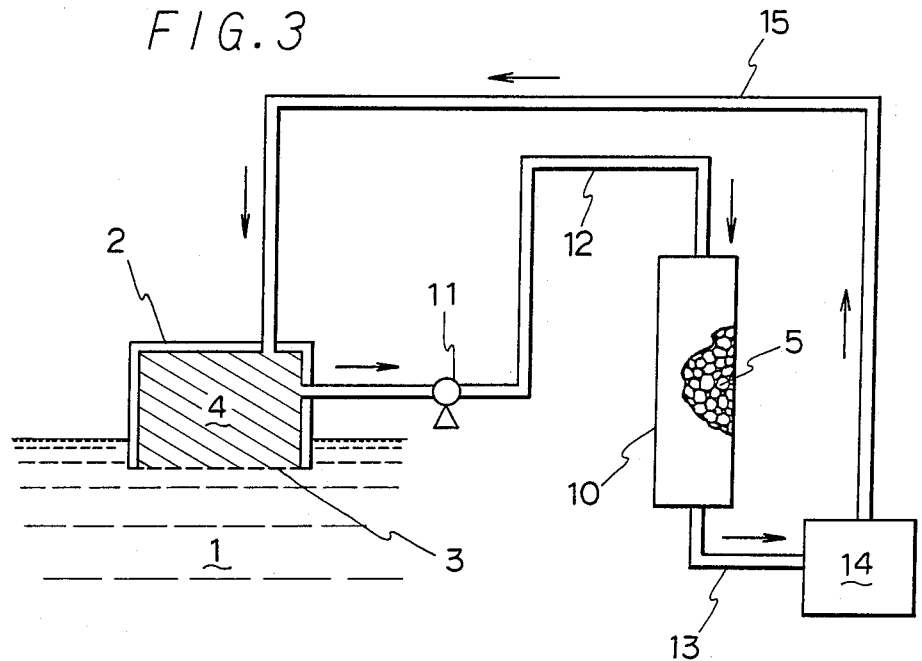

FIG. 3 is another embodiment of the sensor for measuring concentration according to the present invention, which shows an illustration of a circulation type sensor.

In FIG. 3, (1), (2), (3) and (4) represent the liqiud to be measured, the vessel, the membrane and the detecting liqiud respectively. This embodiment differs from the embodiment of FIG. 1 in that it has the ligand (5) filled in the adsorption-desorption member (10), such as a column, set up outside the vessel (2).

In the circulation type sensor, the detecting liquid (4) is transmitted by means of the pump (11) to the adsorption-desorption member (10), where the adsorption to the ligand (5) or the desorption from the ligand (5) of the polysaccharides or of the saccharides to be measured is conducted. Then the detecting liquid (4) which has a changed concentration of the free polysaccharides is transmitted through the pipe (13) to the detector (14), where a change of absorbance is detected. After detection, the detecting liquid (4) is returned to the vessel (2) again through the pipe (15).

The circulation type sensor has advantages such that the part contacting the liquid to be measured can be miniaturalized, the ligand can be maintained at optimum conditions, the amount of the ligand can be increased unrestrictedly, the response can be accelerated, and the like.

Though the circulation rate of the detecting liquid can vary depending on the total amount of the detecting liquid, the amount of the ligand, the section area of the ligand filled layer, mean retention time of the detecting liquid in the adsorption-desorption member, and the like, and may be determined as the occasion demands, the detecting liqiud is usually circulated at from 1 to 10 ml/min with the mean retention time of around 1 to 10 min.

Figure 4:
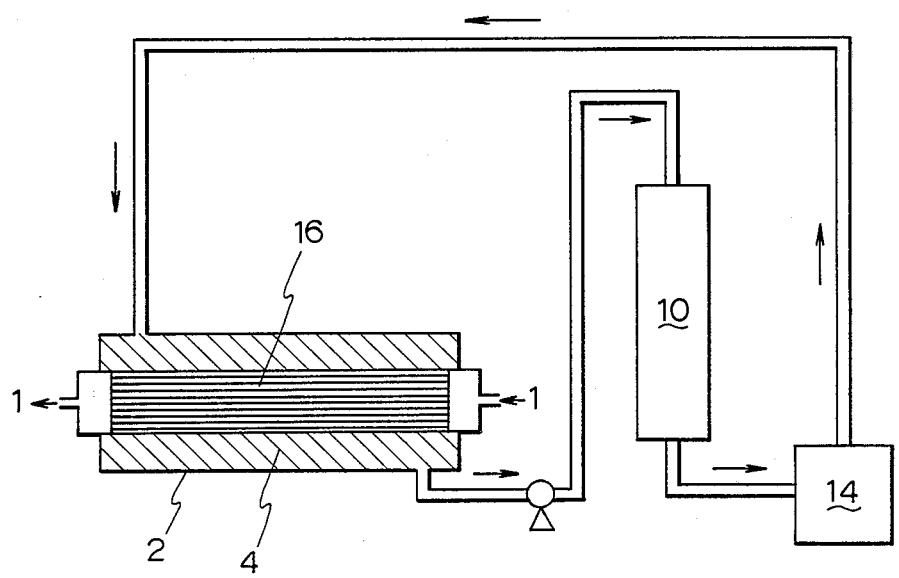

Also the circulation type sensor may be such that the membrane is of hollow fiber and the permeation member is a hollow fiber module (16) as shown in FIG. 4.

The sensor of both types according to the present invention can be employed in places or fields where the sterilization is required since it consists of parts capable of being sterilized especially by a high pressure sterilization.

In FIG. 3 and FIG. 4, the permeation member and the adsorption-desorption member are separately located. However, the ligand may be put in the vessel or filled in the tube or the hollow fiber which constitute the permeation member, and in this case the sensor can be further miniaturalized.

The present invention is more particularly described in the following Examples. However, it should be understood that the present invention is not limited to the Examples and various changes and modifications can be made without departing from the scope and spirit of the present invention.

EXAMPLE 1

The circulation type sensor shown in FIG. 3 was prepared by using the materials as follows:
Vessel: made of glass (content including the pipe: 5 ml)
Membrane: regenerated cellulose membrane (maximum molecular weight which can permeate: $1 \times 10^4$, area: 13 cm$^2$)
Ligand: Concanvaline A-Sepharose (Pharmacia Fine Chemicals Co., Ltd.) 5 ml
Detector: Spectrophotometer 100-10 (made by Hitachi, Ltd., measured wave length: 220 nm)

The detecting liquid was 3 ml of an aqueous solution containing 1 g/l of Blue-dextran 2000 A (made by Pharmacia Fine Chemicals Co., Ltd., mean molecular weight: $2 \times 10^6$), 0.02 mole of Tris(hydroxyaminomethane) and 0.5 mole of NaCl, which was adjusted to Ph 7.4 with aqueous hydrochloric acid solution.

The circulation flow rate of the detecting liquid was adjusted to 2 ml/min by means of the pump.

The membrane side of the sensor was soaked in an aqueous solution of glucose containing 1.5 g/l of glucose, 0.02 mole/l of Tris(hydroxyaminomethane) and 0.5 mole/l of NaCl adjusted to pH 7.4 and the absorbance change of blue dextran was measured with the passage of time. The obtained step response is shown in FIG. 5.

Figure 5:
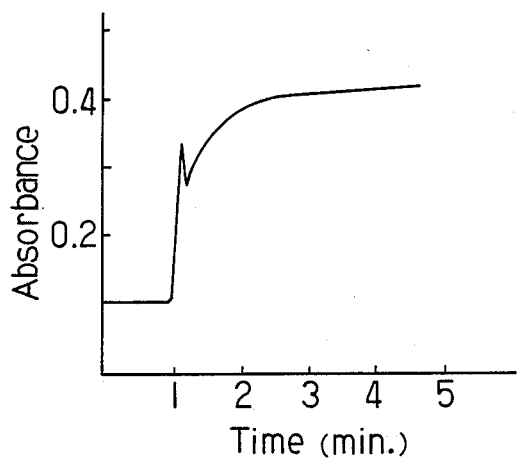
FIG. 5 is a graph of a step response measured in Example 1.

As clearly shown in FIG. 5, the response was observed within several minutes and the output was stable.

EXAMPLE 2

The procedure of Example 1 was repeated except that the concentration of glucose in the aqueous solution of glucose was changed to measure absorbance of the detecting liquid. The obtained result is shown in FIG. 6, as a relation between concentration of glucose and an absorbance.

Figure 6:
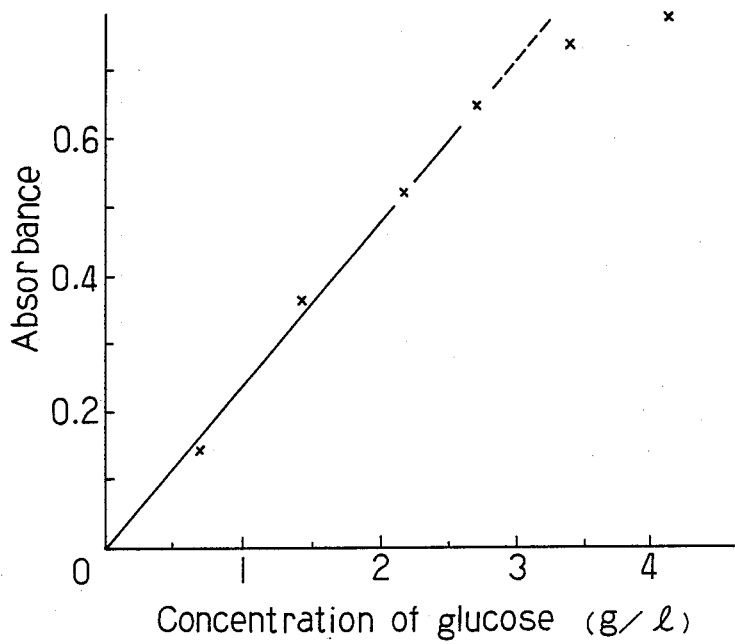
FIG. 6 is a graph showing the relation between concentration of glucose and an absorbance measured in Example 2.

As clearly shown in FIG. 6, the linear relationship was obtained in the suitable range.

What is claim is:

1. A method for measuring the concentration of saccharides having a low molecular weights dissolved in an aqueous medium, said method comprising the steps of:
    (a) bringing a liquid to be analyzed in contact with one side of a membrane provided inside a permeation member, and bringing a detecting liquid in contact with the other side of said membrane inside said permeation member, wherein the detecting liquid contains an aqueous solution of blue dextran, and said membrane allows said saccharides having a low molecular weights to pass through, but does not allow blue dextran to pass through;
    (b) circulating said detecting liquid from the permeation member to come into contact with a ligand provided inside an adsorption-desorption member, wherein said ligand has an affinity for both the saccharides having a low molecular weight and blue dextran, said affinity for the saccharides having a low molecular weight being greater than said affinity for blue dextran;
    (c) measuring the concentration of blue dextran in the detecting liquid by measuring the absorption of light of a selected wavelength by the detecting; and
    (d) calculating the concentration of saccharides having a low molecular weight in the liquid to be analyzed from the change in the concentration of blue dextran in the detecting liquid, said change being due to the adsorption or desorption of said saccharides having a low molecular weight by the ligand and the corresponding desorption or adsorption of blue dextran by the ligand.

2. The method of claim 1, wherein the saccharides having a low molecular weight are those having a mean molecular weight of not more than $1 \times 10^3$.

3. The method of claim 1 or 2, wherein the polysaccharides have a mean molecular weight of not less than $5 \times 10^3$.

4. The method of claim 3, wherein the polysaccharides have a mean molecular weight in the range of from $1 \times 10^4$ to $5 \times 10^6$.

5. The method of claim 1, wherein the ligand is lectin.

6. The method of claim 1, wherein the membrane is an ultrafiltration membrane.

7. The method of claim 1, wherein the membrane is a dialyzer.

8. A circulation-type sensor for measuring the concentration of saccharides having a low molecular weight dissolved in an aqueous medium, said sensor comprising:
    (a) a permeation member;
    (b) a membrane provided inside said permeation member;
    (c) a detecting liquid disposed inside said permeation member on one side of said membrane and containing an aqueous solution of blue dextran, wherein said membrane allows said saccharides having a low molecular weight to pass through, but does not allow blue dextran to pass through;

(d) means for holding a liquid to be analyzed in contact with the other side of said membrane inside said permeation member;

(e) an adsorption—desorption member comprising a ligand, said ligand having an affinity for both the saccharides having a low molecular weight and blue dextran, said affinity for the saccharides having a low molecular weights being greater than said affinity for blue dextran;

(f) means for continuously circulating and conducting the detecting liquid between said permeation member and said adsorption—desorption member; and (g) means for measuring the concentration of blue dextran in the detecting liquid by measuring the absorption of light of a selected wavelength by the detecting liquid.

9. The sensor of claim 8, wherein the permeation member and the adsorption-desorption member are united in one piece.

10. The sensor of claim 8, wherein the detecting liquid further contains an aqueous solution of said saccharides having a low molecular weight.

11. The sensor of claim 8, wherein said adsorption-desorption member is a column.

* * * * *